(12) United States Patent
Siniaguine et al.

(10) Patent No.: US 9,050,211 B2
(45) Date of Patent: Jun. 9, 2015

(54) SELF-ADAPTIVE AND OPTIONALLY ALSO OTHERWISE ADAPTABLE WOUND DRESSING

(76) Inventors: Oleg Siniaguine, Los Gatos, CA (US); Elena Kachiguina, Los Gatos, CA (US)

(*) Notice: Subject to any disclaimer, the term of this patent is extended or adjusted under 35 U.S.C. 154(b) by 502 days.

(21) Appl. No.: 13/402,170

(22) Filed: Feb. 22, 2012

(65) Prior Publication Data

US 2012/0215193 A1     Aug. 23, 2012

Related U.S. Application Data

(60) Provisional application No. 61/463,732, filed on Feb. 22, 2011.

(51) Int. Cl.
  *A61F 13/00* (2006.01)
  *A61F 13/02* (2006.01)
  *A61F 13/15* (2006.01)

(52) U.S. Cl.
  CPC ....... *A61F 13/0226* (2013.01); *A61F 13/15211* (2013.01); *A61F 2013/00246* (2013.01); *A61F 13/00029* (2013.01); *A61F 13/0206* (2013.01); *A61F 2013/00727* (2013.01); *A61F 2013/00855* (2013.01)

(58) Field of Classification Search
  CPC .......... A61F 13/00017; A61F 13/00029; A61F 13/00042; A61F 13/00046; A61F 13/15211; A61F 2013/00246; A61F 2013/00251; A61F 2013/00255; A61F 2013/00259; A61F 2013/0263; A61F 2013/15219; A61F 2013/15227; A61F 2013/15235
  USPC ............................................ 604/364; 602/50
  See application file for complete search history.

(56) References Cited

U.S. PATENT DOCUMENTS

| 5,578,661 | A | 11/1996 | Fox et al. | |
| 5,653,699 | A | 8/1997 | Reed et al. | |
| 5,782,787 | A * | 7/1998 | Webster | 602/46 |
| 7,448,186 | B2 * | 11/2008 | Siniaguine | 53/513 |
| 7,759,537 | B2 * | 7/2010 | Bishop et al. | 602/43 |
| 8,237,007 | B2 * | 8/2012 | Siniaguine | 602/41 |
| 8,362,316 | B2 * | 1/2013 | Kurata | 604/372 |
| 2002/0028232 | A1 | 3/2002 | Kubota | |
| 2008/0132468 | A1 | 6/2008 | Cullen | |
| 2009/0020554 | A1 | 1/2009 | Siniaguine | |
| 2009/0216168 | A1 * | 8/2009 | Eckstein | 602/43 |

OTHER PUBLICATIONS

International Search Report, corresponding to PCT/US2012/026170, Jun. 29, 2012, 12 pages.
Examination Report dated Aug. 14, 2014 in Canadian Patent Application No. 2,826,575.
Examination Report dated Oct. 22, 2014 in Australian Patent Application No. 2012220643.

* cited by examiner

*Primary Examiner* — Lynne Anderson
(74) *Attorney, Agent, or Firm* — Vierra Magen Marcus LLP

(57) ABSTRACT

An automatically self-adjusting variable permeability providing (AVPP) layer is provided over and in operative interaction with a wound site containing a wound to the integumentary system of a living creature such as the skin of a human patient. The AVPP layer has the capability of automatically changing in respective fluid permeability characteristics provided by respective subregions of the AVPP layer where the changes are in reaction to extant or changed conditions in corresponding micro-zones of the wound site. The automatic self-adjusting behaviors of the respective subregions of the AVPP layer can include providing a faster rate of vapor removal for micro-zones of the wound site that are too wet and providing a slower rate of vapor removal or essentially no vapor removal for micro-zones of the wound site that are too dry.

14 Claims, 4 Drawing Sheets

SELF-ADAPTIVE AND OPTIONALLY ALSO OTHERWISE ADAPTABLE WOUND DRESSING

FIELD OF DISCLOSURE AND PRIORITY CLAIM

The present disclosure of invention relates generally to treatment of wounds to the integumentary system of a living creature and more specifically to ongoing treatment of wounds to the skin system of a human being or a like skinned other mammal. The disclosure relates yet more specifically to methods of adaptively controlling the environment of a wound as conditions in and around the wound site change, where the adaptive control is for promoting optimal healing of the wound even as conditions in the wound site change.

This application claims priority from U.S. Provisional Application No. 61/463,732, filed Feb. 22, 2011 by Oleg Siniaguine and Elena Kachiguina, entitled WOUND DRESSING FOR MOIST WOUND HEALING, the entire contents of which application are hereby incorporated by reference.

2a. Cross Reference to Co-Owned Applications

The following U.S. provisional patent application is owned by the owner of the present application, and its disclosure is incorporated herein by reference:
(A) U.S. Provisional Application No. 61/463,732, filed Feb. 22, 2011.

2b. Cross Reference to Issued Patents and Early Published Applications

The disclosures of the following U.S. patents and early publications are incorporated herein by reference:
(A) U.S. Pat. No. 7,910,789, issued Mar. 22, 2011 to Sinyagin; Dmitriy et al. and entitled "Method for treating wound, dressing for use therewith and apparatus and system for fabricating dressing";
(B) U.S. Pub. No. 20110162193 published Jul. 7, 2011 for Sinyagin; Dmitriy and entitled "Method for Treating Wound, Dressing for Use Therewith and Apparatus and System for Fabricating Dressing"; and
(C) U.S. Pub. No. 20100241447 published Sep. 23, 2010 for Siniaguine; Oleg; et al. and entitled "Customization of Wound Dressing Using Rule-Based Algorithm".

3. Description of Related Technology

The present disclosure of invention relates to treatment of wounds to the integumentary system of a living creature and more specifically to wound dressings of the type which can adaptively control the environment or micro-environments within and around a wound site by for example preventing certain parts of a healing wound site from prematurely drying out or getting excessively wet as treatment progresses, while also preventing certain other parts from becoming too dry, whereby such adaptive control of the wound site environment(s) tends to facilitate moist wound healing.

When a wound to the integumentary system of a living mammal (e.g., human being) occurs, the body tends to react differently over time by first, for example, producing relatively large amounts of liquids in and/or around the wound site, where the produced liquids tend to accumulate in the wound and which accumulated liquids are commonly referred to as "wound exudates". Wound exudates may comprise a mixture of different substances including for example, blood, water, salts, proteins, and bacteria. Various studies of the wound healing process have demonstrated that, if kept appropriately physiologically moist in appropriate subregions thereof, a wound tends to heal substantially faster than if it is allowed to become too dry or too wet, especially in the final stages of healing. Such a form of controlled-moisture healing is referred to herein as "controlled moist wound healing".

Traditional wound dressings such as cotton gauze pads and the like operate to deter the escape from the wound site of moisture (water) in a liquid form, but the moisture tends to nonetheless escape in a vapor form (to evaporate into the ambient air) at an uncontrolled and often too rapid rate, which then causes the wound to dry out too rapidly, thus preventing optimal moist wound healing to occur when treated with a conventional cotton gauze pad or the like. Therefore, more advanced wound dressings have been proposed in the art for better controlling the escape rate of vapors from the wound site as well as the escape rate of liquids. However, dressings that are fixed in their design to minimize vapor escape are generally not well suited for appropriately treating wounds with medium to high exudate production rates, where for the latter types of wounds, a faster removal rate of exudate-sourced liquids and/or vapors may be more desirable. At the same time, such fixed design dressings are generally not well suited for appropriately managing the healthy and/or semi-healthy skin that surrounds the open wound site (the peri-wound skin) because exposure to excessive moisture can damage the peri-wound skin and thereby inhibit rather than promote wound healing.

Heretofore, wound treatment specialists have tried to implement controlled moist wound healing protocols by storing on hand, a relatively large inventory of different dressings with respective different sizes and respective different degrees of moisture absorbency, moisture storage capacity and/or vapor permeability. Under this paradigm, the health care providing specialists (specialists in wound care technology) are expected to be frequently checking up on the wound and its healing stage and frequently replacing old dressings with newer and more wound-appropriate newer dressings that address the ever evolving state of the healing (or not-healing) wound. In other words, the wound treatment specialists would attempt on a repeated basis to categorize each individually encountered wound at the time of encounter (e.g., when following up on wound healing progress and changing dressings) and to pick out from their then on-hand inventory of many different kinds of dressings, the dressing that best suites the then identified wound category. There are several drawbacks to this approach. First, the health care providing person who applies the first and subsequent wound dressings needs to be a well trained specialist in wound assessment and treatment. This can be costly. Second, the dressings may need to be changed frequently, which can significantly add to the cost of wound treatment. Additionally, because the human factor is involved, errors may occur in picking out the correct dressing kind each time the dressing is changed. Finally, a large inventory of different kinds of dressings has to be maintained and, if a needed type of fixed-design dressing is depleted from the on-hand inventory, the patient who then needs application of such a specific and fixed design dressing is out of luck.

In general and heretofore, wound treatment dressings were of fixed design relative to spatial and chronological evolution of the individual wound under treatment. Wounds change over time even during one dressing wear. The faster the wound heals, the faster the conditions within the wound site (e.g., exudate production levels, shapes and sizes of various tissue type micro-zones within the wound site, etc.) change under the same dressing. Typically, a wound includes at least three distinct spatial zones or areas whose shapes and sizes tend to change over time. These three major zones are sometimes referred to as the wound bed or wound core, the wound edge and the peri-wound skin which surrounds the wound edge. Healthy skin surrounds the wound edge, and although technically not part of the wound itself, the healthy skin can convert into being part of the wound if the healthy skin is maltreated during treatment of the wound site and its surrounds. The wound bed portion of the wound site is frequently subdivided and categorized into micro-zones or sub-zones, including a heavily exuding sub-zone which exhibits a relatively high intensity of exudate production, a granulating sub-zone horizontal a substantially lower or minimal rate of exudate production, and an epithelializing sub-zone having no appreciable amounts of exudates being produced thereat. Ideally, every such differently categorized tissue sub-zone should be treated with a specifically matched set of treatment parameters (including moisture level parameters). Consequently, for each differently categorized tissue sub-zone, there should be a corresponding wound dressing part that provides the desired treatment parameters for thereby implementing an optimal local micro-environment for the respective tissue sub-zone. More specifically, each heavily exudating part of the wound site should be overlapped by a wound dressing region which provides relatively high levels of liquid absorption and relatively high rates of vapor release (evaporation) into the ambient air. The high rate of vapor release is desired in order to avoid accumulation of excessive amounts of liquid in the heavily exuding part of the wound, where such accumulation tends to be detrimental to optimal healing. On the other hand, each low or non-exuding wound part needs to be kept moist but never (or hardly ever) too wet. Excessive drying out (undue desiccation) should be avoided, for example by designing the corresponding wound dressing region to prevent or minimize water vapor loss in the slow and/or not-exuding zones. These exemplary design requirements demonstrate how the needs of one sub-zone of a wound site can contradict those of another and yet the different sub-zones and their opposed needs typically coexist simultaneously in and around a single wound site.

As time goes by and the wound progressively heals (or as it progressively gets worse if for example appropriate antibiotics have not been applied or if it is unexpectedly re-injured) the zonal geographies and/or rates of exudate production and/or degrees of epithelialization of the wound site can dynamically change and, ideally, the dressing should be reconfigured to address these changes in timely fashion. However, heretofore, the state of the art in wound dressings did not provide an economical and practical means for addressing the divergent zonal treatment requirements typically found in and around a typical wound and it did not provide an economical and practical means for addressing the over-time, and sometimes rapid state changes that may occur in different sub-zones of the wound site. One example of an unexpected rapid state change in a wound is if the patient accidently bumps the wound site (with old dressing on it) into a sharp object and thereby re-injures the wound site.

The unexpected extreme injury to the wound site is but one example of how a dressing with fixed design may cease to provide appropriate healing-promoting micro-environments for respective micro-zones of an unexpectedly variable wound site. When a clinician inspects an encountered wound site for the purpose of formulating a treatment-appropriate dressing design for the wound, the clinician is merely seeing an out-of-the-field snapshot of the wound and of the patient to whom the wound belongs. At the time of clinical observation, the patient may be unusually anxious and this anxiety may lead to the wound exhibiting more than normal levels of exudate production. Once the patient leaves the clinic, he or she may calm down and the level of exudate production may then decrease as a result. However, what that generally means is that the clinician was induced by the distorted snapshot and in-clinic observation of the wound to provide a wound dressing that provides too fast of a drying action for the wound once the latter gets back into the field and the wound therefore heals at less than optimum rate or not at all because micro-zones therein are too dry.

On the other hand, it equally possible that the patient is less anxious or less agitated while in the clinic and wound exudates less than usual during the clinical preparation of the dressing. Once the patient gets out into his or her more normal world (the out-of-clinic normal routines), the patient may become more anxious or agitated due to work stresses for example or exercise routines and then the wound begins to exude at faster rates than were observed in the clinic. What this generally means is that the clinician was induced by the distorted snapshot and in-clinic observation of the wound to provide a wound dressing that provides too slow of a drying action for the wound once the latter gets back into the field. Therefore, once again, the dressing design that was fixedly set in the clinical environment provides a non-optimal treatment for the in-field wound. Other examples where the states of various micro-zones within the wound site may change can include ones where the patient consumes alcohol and/or various prescription drugs or other substances after leaving the clinic and these consumptions alter the state of the wound. Another example of where exudation rates can change is if the patient's blood pressure substantially rises for any of a number of reasons or instead falls below the levels present during the clinical visit. Yet another example of where exudation rates can change is if the patient's wound unknowingly got infected while at the clinic and the consequence of the infection does become apparent until long after the patient has left the clinic. At that point, because no one sees what is going on under the dressing, the changed conditions of the wound go undetected and untreated.

Given the above, it appears that wound treatment could be made much more economical and practical if a self-adaptive wound dressing could be developed which, not only at the time of initial application, appropriately and respectively absorbs exudates or hydrates at respective different rates at respective wound sub-zones (micro-zones) that need the respective rates of liquid absorption and vapor release into the ambient, but also that later on, automatically and adaptively self-adjusts to match changing wound conditions at respective sub-zones of the wound site and/or self-adjusts to match changing dimensions of such sub-zones while providing appropriate micro-environments for optimal promotion of healing for the respective sub-zones having the various wound tissue types, including for the wound edge subregions, and the peri-wound skin sub-zones. Additionally, wound treatment could be made much more economical and practical if the dressing is designed to assure that healthy skin surrounding the wound site is not damaged by the dressing. One advantage of an automatically self-adjusting adaptive wound dressing is that the persons applying the dressing to the wound (e.g., health care practitioners) would not have to be sophisticated experts in the art of selecting appropriate wound dressing materials (having appropriate treatment characteristics) and appropriately shaping and dimensioning them, and appropriately aligning them to respective portions of the wound site. Instead, they would simply apply the blankslate wise, initially pre-configured dressing to the wound site without worrying about specific alignment and then the self-adaptive dressing would automatically and in concert with the encountered wound site conditions, automatically configure itself by appropriately altering material characteristics within the dressing to match the therapeutic needs of the then encountered underlying micro-zones within the wound site in such a way that the re-configured material zones automatically align with the underlying micro-zones. Moreover, because the self-adjusting adaptive wound dressing continues to re-adjust itself to ever changing conditions within the wound site, the person(s) who apply the dressing would not have to change dressings as often; and also they would not have to keep as large an inventory of different dressings as they now have to keep on hand because an automatically self-adjusting adaptive wound dressing would custom-tailor itself to the unique needs of each encountered and unique wound (and its unique interior subregions) without calling for subjective human judgment. The self-adjusting adaptive wound dressing would automatically follow along with and self-adapt to the unpredictable changes in the wound site during the duration of application of the dressing. As mentioned above, one example of an unpredictable change in the wound site during the duration of a dressing wear is if the patient accidently bumps the wound site (with old dressing on it) into a sharp object and thereby re-injures the wound site whereby one or more wound site subregions that were previously non-exuding ones suddenly become heavily exuding ones due to the new injury inflicted on the otherwise healing wound site. A conventional dressing that is not self-adaptive could not automatically and relatively immediately respond to such suddenly changed conditions.

It is to be understood that this background of the related technology section is intended to provide useful background for understanding the here disclosed technology and as such, the technology background section may and probably does include ideas, concepts or recognitions that were not part of what was known or appreciated by those skilled in the pertinent art prior to corresponding invention dates of subject matter disclosed herein.

SUMMARY

In accordance with one aspect of the present disclosure of invention, an automatically self-adjusting variable permeability providing (AVPP) layer is provided over and in operative interactive coupling relation with a wound site containing a wound to the integumentary system of a living creature such as the skin of a human patient. The AVPP layer has the capability of automatically changing in respective fluid permeability characteristics provided by respective subregions of the AVPP layer where the changes are in reaction to extant or changed conditions in corresponding micro-zones of the wound site. The automatic self-adjusting behaviors of the respective subregions of the AVPP layer can include providing a faster rate of vapor removal for micro-zones of the wound site that are too wet and providing a slower rate of vapor removal or essentially no vapor removal for micro-zones of the wound site that are too dry. The automatically self-adjusting variable permeability providing (AVPP) layer may form part of a wound treatment dressing applied to an underlying wound site. The dressing may additionally include a liquid-impermeable but vapor breathing (LIVB) layer disposed above the AVPP layer and a liquid absorbing layer or pad disposed under the AVPP layer. In operation, the liquid absorbing layer transmits to respective subregions of the AVPP layer, fluids that, if present, are indicative of tissue states of the micro-zones of the underlying wound site and the AVPP layer automatically and self-adjusting wise provides corresponding fluid permeability characteristics for appropriately keeping the respective micro-zones as not too wet and not to dry for sake of promoting healing of the wound.

BRIEF DESCRIPTION OF THE DRAWINGS

The below detailed description section makes reference to the accompanying drawings, in which.

DETAILED DESCRIPTION

Figure 1:
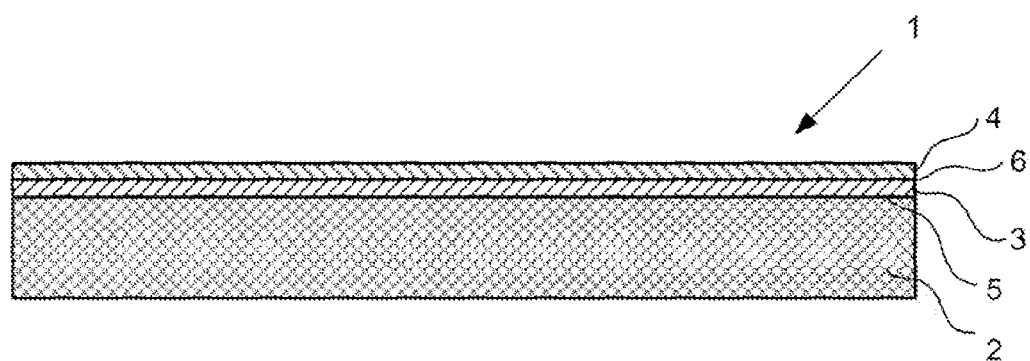
FIG. 1 is a schematic cross sectional view of an automatically adaptive (and optionally manually further adaptable) wound dressing according to one aspect of the present disclosure of invention.

With regard to the figures, it is to be appreciated that these are not to scale and the illustrated thicknesses are generally exaggerated relative to the illustrated lateral widths of the dressings. The terms, upper and lower will be used herein as relative terms that are applicable to the case where the dressing is positioned as shown in the drawings with one layer being disposed above a next and so forth. Flipping the dressing upside down or otherwise (e.g., at other angles) does not alter the relative, upper versus lower; or above versus below designation given herein to the various layers. Similarly when various fluids are stated herein to be drawn "up" for example or spread out "laterally" (horizontally) for example, those designations are also to be understood as relative terms. Flipping the dressing upside down or otherwise (e.g., at other angles) does not alter the relative, up versus down; or lateral versus vertical designations given herein to the various fluid flow directions.

Referring to FIG. 1, a first example of an automatically adaptive wound dressing 1 in accordance with the present disclosure is depicted therein by an exemplary cross sectional view. The from-the-above top plan view (not shown) may take on many different shapes, dimensions or configurations that generally comport with the illustrated and exemplary cross sectional view of FIG. 1, where the latter cross sectional view may be taken along a desired sectioning line or sectioning curve drawn on the top plan view (not shown). More specifically, in FIG. 1 the dressing 1 is shown to comprise a liquid(s) adsorbing pad 2, a first vapor permeable layer 3 and a second vapor permeable layer 4 stacked over one another in the recited order. Of importance, in the various embodiments the first and second vapor permeable layers 3 and 4 are not of identical function. The first vapor permeable layer 3 may be made permeable to liquids (e.g., liquid water) as well as being permeable to vapors (e.g., water vapor) while the second vapor permeable layer 4 is not permeable to liquids. Both of the first and second vapor permeable layers, 3 and 4 may be made impermeable to molecules and/or to particles substantially larger than H2O molecules, for example to bacterial cells or cell fragments. Although the first and second layers, 3 and 4, are frequently referred to herein as vapor permeable layers, from time to time the second layer 4 will also be referred to as a "liquid-impermeable but vapor breathing" (LIVB) layer 4. On the other hand, the first mentioned layer 3 will also be referred to herein as an "automatically-variable permeability providing" (AVPP) layer 3 for reasons that will shortly become apparent.

The absorbent pad 2 is permanently (nondetachably) attached to at least one of the first and second vapor permeable layers, 3 and 4, and in the illustrated case of FIG. 1 it (2) is shown to be so attached to a lower first side 5 of the first vapor permeable layer 3. The second vapor permeable layer 4 (a.k.a. the liquid-impermeable but vapor breathing (LIVB) layer 4) is bonded to an upper second side 6 of the first vapor permeable layer 3. In one embodiment, parts (e.g., removable strips or dots) of the upper or second vapor-permeable/liquid-impermeable layer 4 (LIVB) are detachably bonded to the underlying layers or films and may be manually and/or by machine-means, selectively removed (e.g., by scratch or peel-off removal) so as to thereby alter local fluid (vapor) exhaust rates there-at.

In the same or another embodiment, parts (e.g., micro-zones) of the first vapor permeable layer 3 (a.k.a. the automatically-variable permeability providing (AVPP) layer 3) are time-release wise and/or concentration of exposure-wise changed by having been exposed to a change-triggering concentration or amount of moisture (e.g., a vapor and/or liquid that triggers chemical change in AVPP layer 3) whereby, at first; before they are exposed to a sufficient amount of moisture, the respective micro-zones will exhibit a comparatively low rate of vapor transmission (a low MVTR, as shall be defined below) but after having been exposed over time to a sufficient amount of moisture (e.g., a sufficient concentration of a particular type of liquid for a sufficient length of time), they will exhibit a comparatively higher rate of vapor transmission (higher MVTR) so to thereby automatically increase a moisture-removal rate provided for the wound site tissue below them. And then later, after local moisture concentration drops below a predetermined level, the variable parts (micro-zones) of the first vapor permeable layer 3 (the AVPP layer) will revert to exhibiting a comparatively lower rate of vapor transmission (lower MVTR) so to thereby automatically prevent excessive drying out of the wound site sub-zones below them after a desired amount of local moisture-removal has occurred. This low, high, and then low-again vapor transmission rate behavior is particularly useful for proper treatment of the peri-wound skin and epithelializing parts of the wound site. The latter two parts should be progressively growing inward towards the center of the wound site while the respective moisture levels in those respective sub-zones are kept optimal for those zones to keep growing inwardly and thus continue the healing process. More specifically, the outer periphery of the peri-wound skin zone generally calls for a drier but not arid micro-environment while the zones inward of the peri-wound skin zone typically call for a wetter micro-environment. During healing, the boundary between the two zones advances (travels) inwardly as the wound heals and thus the optimal but different micro-climates for the two zones should spatially advance inwardly with their respective wound site zones.

The liquid absorbing pad 2 operates to draw excessive exudate away from the wound site and to store components (e.g., drawn up bacterial cells) of the removed exudate apart from the underlying wound site. The liquid absorbing pad 2 may include one or more of hydrophilic fibrous or foam materials which can readily absorb (bind to them) substantial quantities of water or aqueous solutions and store drying out components of the absorbed and drawn up liquids. The pad 2 preferably comprises a non-woven fabric such as an air-layered or meltspun or electrospun rayon or polyester, or polyvinyl alcohol (PVA) and/or its ethylene copolymers, or other hydrophilic synthetic or natural polymers and materials useful for adsorption and absorption of substantial quantities of water or aqueous solutions. The absorbent pad 2 may contain embedded gelling fibers or particles (globules) of super-absorbent polymers (e.g., polyacrylamide or polyacrylate such as those marketed by Emerging Technologies, Inc., Greensboro, N.C.) or other known hydropolymers that bind water (e.g., alginates, reprocessed cellulose, crosslinked or high molecular weight polyethylene oxide, polyvinylpyrrolidone). The absorbency of the pad material is preferably at or higher than 10 grams-of-absorbed liquid per gram of absorbent ($\geq 10$ g(L)/g(A)) for, for example, a 0.9% sodium chloride and calcium chloride solution that is considered to be close to the composition of typical wound exudate. Absorption Capacity may be measured according to the DIN EN 13726-1 standard. In one embodiment, the absorbency of the pad material progressively increases as one moves upwardly (e.g., in the +Z direction) in the cross-sectional view of FIG. 1 whereby the effect is that initially encountered exudates are rapidly drawn up and away from the wound site for storage in, and for drying out within the upper parts of the liquid absorbing pad 2 while later encountered exudates (e.g., those with fewer amounts of bacteria and/or dirt) are more slowly drawn up into the lower sections of the pad 2. One of the reasons that slower absorption rates may be desirable after initial absorption of exudates is so that the micro-environment of the underlying wound zone does not become too dry after the initially large amount of exudate has been taken up. In one embodiment, the absorbent pad 2 exhibits a directional absorption preference that favors drawing liquids more so in the upward direction (e.g., in FIG. 1) rather than laterally so that liquids drawn up from a first sub-zone of the wound site tend to not flow laterally through the absorbent pad 2 and thereby appear to higher layers (e.g., 3 and 4) of the dressing as if the liquids had instead been drawn up from a laterally spaced apart, other sub-zone of the wound site.

The absorbent pad 2 material may include antimicrobial additives, like broadly used silver and silver salts, polyaminopropyl biguanide (PAPB), polyhexamethylene biguanide (PHMB), polyhexamethylene guanide or polyhexanide, or other known in the art antimicrobials, antiseptics and/or preservatives in known and recommended for use concentrations that are non-cytotoxic, typically 0.01-0.5% by weight.

The absorbent pad 2 may include embedded hygroscopic liquids for providing a desired degree of fiber and/or particle softening so that the dressing can easily flex when applied to the wound site. Preferably, the embedded hygroscopic liquid is polypropylene glycol or glycerin. The amount of hygroscopic liquid is preferably 0.001-0.05 g/cm$^2$, and more preferably 0.005-0.03 g/cm$^2$.

The absorbent pad 2 may initially be pre-charged with an embedded quantity of sterile water (or saline solution) for irrigating and moisturizing the wound site at an initial stage of wound treatment. The amount of water in the absorbent pad 2 may be about 50-80 weight %. Preservatives like benzyl alcohol 0.9% or 0.085% chlorhexidine gluconate or 0.02% bronopol may be added to the water pre-charge. In one embodiment, the pre-charged irrigation liquid(s) is/are stored in pressure frangible beads which break open when sufficient pressure is applied to them. More specifically, the user may be instructed to knead the packaging that holds the dressing before taking out the dressing and applying it to the wound site. (See for example US Pub 2007/0020320 "Wound dressing and methods of making and using the same", David et al which is incorporate herein by reference.)

The absorbent pad 2 may initially be pre-charged with an embedded mixture of water and hygroscopic liquid. The percent of hygroscopic liquid in the water-glycerin mixture may be about 5-75% w (by weight), and more preferably 10-30% w. The amount of water-hygroscopic liquid mixture initially provided within the absorbent pad 2 may depend on the percentage of hygroscopic liquid in the mixture, and may be such that the resulting amount of water in the absorbent pad 2 is 10-80 weight %. The resulting amount of water or aqueous solution initially provided within the absorbent pad 2 may be less than the maximum absorption capacity of the absorbent pad 2. One function of such an initially provided pre-charge of water or aqueous solution may be to irrigate the wound site with sterile liquid prior to or at the same time as beginning to absorb exudate. As indicated above, the initial irrigating liquid(s) may be stored in frangible beads or the equivalent embedded within the absorbent pad 2 and released when the pad is kneaded by hand or by appropriate machine means.

The absorbent pad's vertical thickness and lateral length and width dimensions may vary depending upon the intended use for the dressing. The thickness of the absorbent pad 2 may be between 1 and 3 mm or thicker, preferably 1.5-2 mm. The dressing is typically made in a range of sizes: 5×5 cm, 10×10 cm, 15×15 cm, 20×20 cm as measured in the lateral directions. Therefore the lateral dimensions are substantially larger than the vertical thickness. The shape of the absorbent pad (as seen in the top plan view) may be rectangular or oval or another shape specifically applicable to a particular part of a human body where the dressing is to be applied to. In use, the lower major surface of the absorbent pad 2 engages directly or indirectly with the wound site while the second vapor permeable layer 4 (the liquid-impermeable but vapor breathing (LIVB) layer) interfaces with the exterior air. The serial combination of the first and second vapor permeable layers, 3 and 4, controls the rate of vapor exhaust from the interior of the dressing and into the ambient air. The upper vapor permeable layer 4 may optionally have parts that can be selectively detachably removed from the lower vapor permeable layer 3 (or from lower film layers of the second vapor permeable layer 4 itself) in the form of rectangular strips or circular ones of concentric rings or otherwise so that, for example, quick detach removal or scratching away of more central and upper film parts of the upper vapor permeable layer 4 (e.g., those at or closer to the central surface area of the dressing) will result in a dressing that has higher rates of vapor exhaust nearer to the central and more heavily exudating core of the wound site while initial non-removal of the more peripheral strips or rings of the upper vapor permeable layer 4 result in a dressing that has lower rates of vapor exhaust at or near the peripheral areas of the wound site (e.g., above the peri-wound skin and surrounding healthy skin). As time progresses, the outer removal rings (of layer 4) may be progressively removed to promote further drying around the outer periphery of the peri-wound area as the latter advances (grows) inwardly during the course of typical wound healing. In one embodiment, a scratch-resistant, but fluid passing mesh (not shown) is interposed between a top and optionally detachable film of the vapor-permeable/liquid-impermeable layer 4 and a lower but not detachable film of the same layer 4 (films not separately shown). The optional, scratch-resistant mesh (not shown) protects the lower film from being removed even as the upper one is scratched or peeled away. In this way, the general liquid-impermeable but vapor breathing (LIVB) properties of the second vapor permeable layer 4 are substantially preserved.

Figure 2:
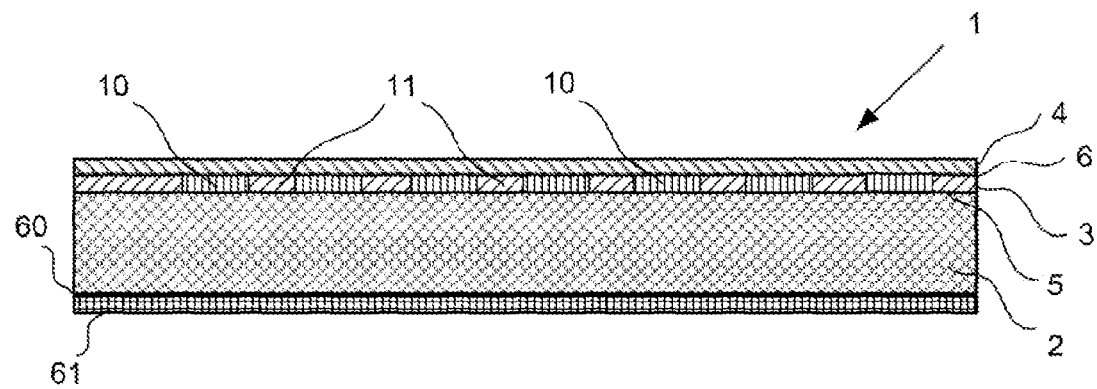
FIG. 2 is a schematic cross sectional view of another embodiment having first and second vapor permeable layers where at least one of the vapor permeable layers exhibits an adaptively programmable MVTR profile.

In another embodiment (FIG. 2), the wound-facing bottom side 60 of the absorbent pad 2 is covered with a wound-contacting layer 61, where the wound-contacting layer 61 rather than the absorbent pad 2 defines a directly wound-contacting face of the dressing. The wound-contacting layer 61 is permanently (e.g., nondetachably) attached to the absorbent pad 2. The wound-contacting layer 61 may be made of a pre-sterilized liquid permeable mesh or perforated film or liquid permeable non-woven fabric. The wound-contacting layer 61 should be made of a material that is biocompatible with the wound site and may be made of a synthetic or biologic or bioabsorbable polymer or their combinations. Examples of such polymers include nylon, polyethylene, polyvinyl alcohol (PVA), ethylene vinyl acetate and/or ethylene vinyl alcohol copolymers, which are typically nonadherent to the wound tissue. The wound-contacting layer 61 should be perforated or porous to allow for the passage therethrough of wound moisturizing liquid and/or exudate liquid and/or wound moisturizing vapor. The thickness of the wound contact layer 61 may be in the range of about 5-500 microns and the pore size may be in the range of 0.1-1000 micron. The wound contact layer 61 material may include antimicrobial additives, like broadly used silver and silver salts, polyaminopropyl biguanide (PAPB), polyhexamethylene biguanide (PHMB), polyhexamethylene guanide or polyhexanide, or other known in the art in concentrations that are non-cytotoxic, typically 0.01-0.5% w.

In one embodiment, the whole of the automatically-variable permeability providing (AVPP) layer 3 is at least partially or completely soluble in water and/or in specific other liquids such that if respective sub-portions of layer 3 are exposed to wet exudate for example, the respective sub-portions will partially (e.g., proportionally) or fully dissolve into the surrounding liquid and thereby automatically create corresponding areas of increased vapor permeability (faster vapor escape rates) in the dressing. In an alternate embodiment, first vapor permeable layer 3 (e.g., that of FIGS. 1 and 2) instead includes spatially distributed material spots 10 that are at least partially or completely soluble in water and/or in specific aqueous liquids such that if they are exposed to wet exudate for example, they will partially (e.g., proportionally) or fully dissolve into the surrounding liquid and thereby automatically create corresponding areas of increased vapor permeability (faster vapor escape rates) in the dressing. Other portions (11) of the automatically-variable permeability providing (AVPP) layer 3 are not dissolvable or substantially less easily dissolvable. The dissolving of the spots 10 and/or respective sub-portions of the automatically-variable permeability layer 3 need not create a through hole at the spot (e.g., 10) where the dissolving occurs but rather such dissolving may instead create a region of reduced film thickness. Such reduced film thickness correlates with a higher MVTR. Additionally, the dissolving of the spots 10 and/or respective sub-portions of layer 3 to the point where through holes are created may cause the lower or first vapor permeable layer 3 to become permeable to liquids as well as to water vapor. This occurs if the amount of dissolution at spots 10 (or other dissolvable sub-portions of layer 3) is large enough to create through holes. In other words, liquid permeability is induced when the local concentration of a hydrolyzing liquid (e.g., exudate) is sufficiently high and is present for a sufficiently long time (and optionally also has a required level of acidity or other chemical attribute) to completely eat through a significant portion of hydrolyzable polymer bonds present at that spot 10 (or other alike sub-portion). Examples of materials which can be tailored to have such characteristics include polyvinyl alcohol (PVA), poly ethylene oxide, poly vinyl pyrrolidone and other known polymers and/or their blends or co-polymers with various degrees or cross-linkage breakability or hydrolyzation-ability being integrated into the characteristics of the picked polymer. As used herein, the "degree" of cross-linkage breakability or hydrolyzation-ability measures the proportion of locally present polymer bonds that can be broken by a corresponding hydrolyzation process. (As understood in the chemical arts, hydrolyzation is a chemical process resulting in bond decomposition, where the process involves the splitting of the bond and the addition to, or substitution at the location of the broken bond of a hydrogen cation and a hydroxide anion in place of the bond; where the $H^+$ and $OH^-$ substitutes may be obtained from surrounding water molecules for example.)

The first vapor permeable layer 3 may be made in the form of a non-porous film (a solid film through which gases may diffuse but liquids cannot flow) having alternating spots 10 of hydrolysable (soluble) material and surrounding mesh areas 11 of non-hydrolyzable (non-soluble) material each with a thickness of about 25-300 microns. In embodiments where upper film strips of upper layer 4 are additionally, optionally detachable, the detachable upper portions preferably overlap only the non-dissolvable mesh portions 11 of the lower, first vapor permeable layer 3 so that open holes (for bacteria to get in) will not be created by combined complete dissolution of the hydrolyzable material spots 10 of the first vapor permeable layer 3 and optional detachment of the detachable portions of the upper, second vapor permeable layer 4.

Figure 5:
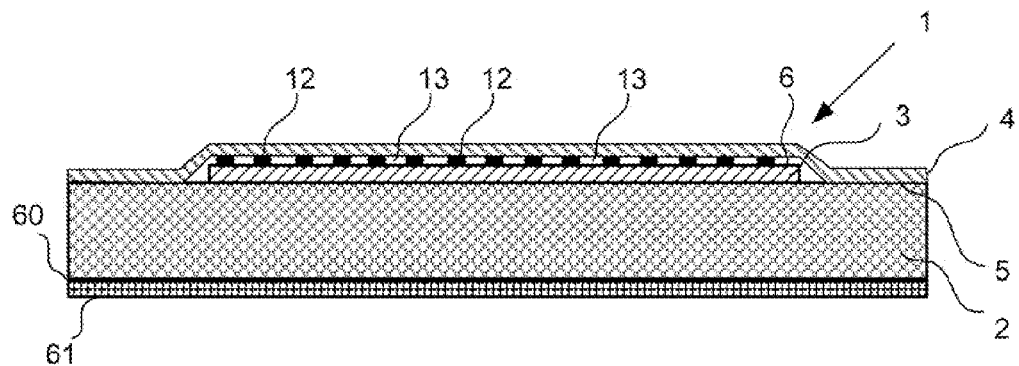
FIG. 5 is a schematic cross sectional view of another embodiment having a spacer disposed between the first and second vapor permeable layers.
Figure 6:
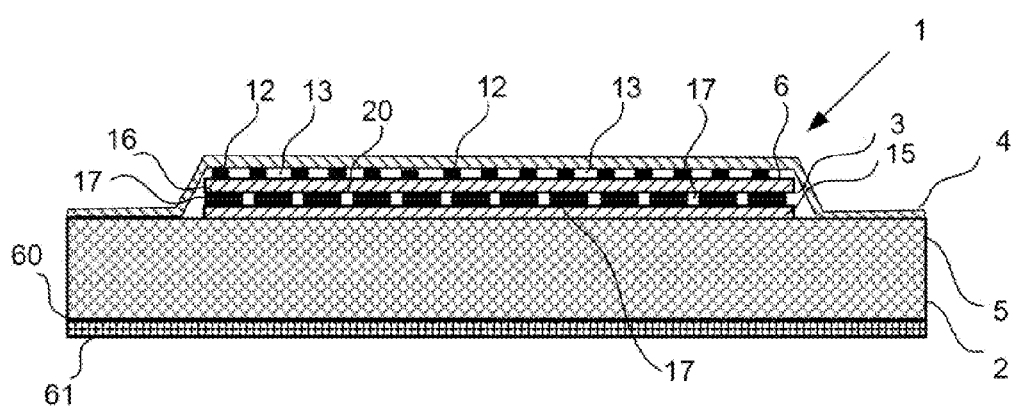
FIG. 6 is a schematic cross sectional view of another embodiment having a third vapor permeable layer.

The first vapor permeable layer 3 (the automatically-variable permeability providing (AVPP) layer 3) may be made of the above-mentioned materials which initially have relatively low Moisture Vapor Transmission Rates (MVTR) such as <1000 g/m2/24 Hour, preferably <500 g/m2/24 H, when the material is dry (it has not yet been exposed to a hydrolyzing liquid), and it has a substantially increased MVTR, for example >1000 g/m2/24 Hour when the material has been exposed to a hydrolyzing solution (e.g., exudate) for a sufficiently long time duration. Therefore subregions of the dressing that are exposed at layer 3 to exudate absorbed thereto from a corresponding subregion of the wound site and for long enough of an exposure period will adaptively and automatically convert to dressing subregions of relatively higher vapor transmission (e.g., MVTR>1000 g/m2/24 Hour) while subregions of the dressing that are not exposed at layer 3 to large concentrations of exudate absorbed thereto from a corresponding subregion of the wound site and/or for not long enough of an exposure time will remain substantially in their initial and relatively low MVTR state (e.g., MVTR<500 g/m2/24 H). In other words, the dressing automatically and adaptively self-adjusts according to the degree of exudate absorbed from each respective micro-zone of the wound site and transmitted to a corresponding hydrolyzable material spot (e.g., spot 10) of the first vapor permeable layer 3. In one embodiment, the lower, first vapor permeable layer 3 also automatically becomes increasingly more permeable to small-sized liquid molecules (e.g., H2O) when exposed over time to sufficient concentrations of a hydrolyzing solution (e.g., exudate). The advantage of this aspect will be discussed when the spacer-including embodiments of FIGS. 5 and 6 are discussed later below.

MVTR (Moisture Vapor Transmission Rate) may be measured according to the DIN EN 13726-2 standard. (DIN is a German abbreviation which in English means the German Institute for Standardization.)

In one embodiment, the dissolvable spots 10 of the first vapor permeable layer 3 include temperature-dependent spots 10 which are made of one or more materials that are soluble only in above-room-temperature water or aqueous solution with a temperature for example that is >25° C. More specifically, the hydrolyzing solution (e.g., exudate) may be heated to above normal room-temperature by the patient's body heat (and/or by another heat providing means—e.g., an electric heating element). An example of such a temperature-sensitive material may be polyvinyl alcohol (PVA) with 60-80% degree of hydrolyzation, where here, the percent of hydrolyzation indicates what proportion of available polymer bonds are broken by prolonged exposure at temperature to the hydrolyzing solution.

The upper or second vapor permeable layer 4 may be made of a nonporous film or non-woven fabric with a relatively low moisture vapor transmission rate (MVTR) or it may be made of multilayer combinations of non-woven fabric and nonporous film materials permanently and/or detachably bonded together to provide a desired MVTR for that second vapor-permeable/liquid-impermeable layer 4. The thickness of the second vapor permeable layer 4 may be in the range of about 10-150 microns, or more preferably 50-100 microns. The material of the second vapor permeable layer 4 may include polyethylene, polypropylene, polyester and/or poly vinyl acetate.

Of importance, the upper or second vapor permeable layer 4 should be made of a liquid impermeable and microorganism impermeable material that nonetheless transmits vapor with an MVTR >1000 g/m2/24 H. By contrast, the lower or first vapor permeable layer 3 may be composed of one or more materials that, when converted by hydrolyzation; do permit small sized liquid molecules (e.g., H2O) to permeate through them but preferably still block larger sized particles (e.g., microorganisms) from permeating through.

Laminations of thin polyurethane films may be used to meet the above preferred characteristics for the second vapor permeable, but liquid impermeable layer 4. The films of layer 4 may each have a thickness of about 10-50 microns and may provide MVTR's up to 3000 $g/m^2/24$ hours depending on composition and thickness. Preferably, the film or films for second layer 4 is/are chosen to exhibit an MVTR greater than 2000 $g/m^2/24$ hrs while still being impermeable to liquids. In one embodiment, if multiple films are used for forming the second vapor permeable layer 4, they are provided with respective different colors, for example red and blue with the blue covering the red (and a scratch resistant mesh being optionally interposed between). A user may scratch off or otherwise selectively remove the upper and first colored film to thereby expose the lower and differently colored film of the liquid impermeable layer 4 (optionally through a see-through scratch resistant mesh). By this means, the user (e.g., health care provider) can readily see what pattern of selective increase of MVTR for water vapor is being provided by the manually programmed (or machine-wise automatically programmed) selective removal of part of the top of layer 4. In one embodiment, an exposed red color is understood to mean a higher MVTR while blue indicates a lower rate.

Hydrophobic non-woven fabrics and micro-porous membranes (e.g., those marketed by the 3M™ Company) with pore sizes of 0.1 micron or less are also micro-organism impermeable and resistant to passing water and water based liquids but provide relatively high MVTR due to their open micro-pore structures. Polypropylene or other hydrophobic polymers may be the material of choice for non-woven layer or micro-porous membrane. Typical thickness of the non-woven film for layer 4 or a membrane thereof is 50-500 microns.

The second vapor permeable but liquid impermeable layer 4 may be made as a multi-layer stack of films and non-woven fabrics permanently or detachably bonded together (not shown in Figs). Such stacks may help minimize the inconvenience of thin film handling but still preserve the desired high MVTR rating for the second layer 4.

The first vapor permeable layer 3 is preferably bonded to the absorbing pad 2 with a porous adhesive (not shown on the Figs.) where the porous adhesive has open cell pores after curing and thus allows for passage of liquid therethrough. The pore size of the cured adhesive may be 0.1-200 microns. The more preferred pore size is 0.1-10 microns. (An example of such an open pore adhesive is a porous adhesive marketed by Adhesive Research, Inc., Glen Rock, Pa.).

It will be appreciated that the vapor permeable layers 3, 4, the absorbent pad 2 and wound contact layer 61 could be manufactured and/or later cut to have any suitable shape and dimensions such as 3×5 inch rectangular, circular, oval, triangular or other specific to a particular part of a human or animal body and the shape and size of the wound site.

Other adaptive dressings in accordance with present disclosure of invention may comprise one or more additional vapor permeable layers placed on top of and/or below the second vapor permeable layer 4. The additional layers may have the same or similar features as said second vapor permeable layer 4, including optional, non-automatic (e.g., manual) programming of the MVTR in different areas of the dressing's upper surface.

The respective outer perimeters of the absorbent pad 2 and the first and second vapor permeable layers 3 and 4 may be laterally coextensive with one another, i.e., vertically superimposed (see FIGS. 1-2), so that the entire upper surface area of the absorbent pad 2 is covered in the lateral directions by the first and second vapor permeable layer 3 and 4. In a variation, the peripheries of one or both of the first and second vapor permeable layers 3 and 4 may extend beyond the lateral periphery of the absorbent pad 2 so that sidewalls of the absorbent pad 2 are covered by at least one of layers 3 and 4.

The permanent attachment of the absorbent pad 2 to the first vapor permeable layer 3 can be made by lamination, or by extruding the film material of layer 3 directly onto the absorbent pad 2 material, or by electrospinning of fibrous material of the absorbent pad 2 directly on the material of the first vapor permeable layer 3. If lamination is employed, the lower, first side 5 of the first vapor permeable layer 3 may be coated with a pressure sensitive (pressure activated) adhesive (not shown in the Figs.). This attachment adhesive should have an MVTR that is not less than the MVTR of the first vapor permeable layer 3. That may be achieved by using a patterned adhesive with >50% of the open area. (An example is a patterned pressure sensitive adhesive, marketed by SCAPA, Inc. of Inglewood, Calif.)

As mentioned above, some segments or spots 11 of the first vapor permeable layer 3 may be made non-soluble (FIG. 2) to water or aqueous solutions. This may be achieved by patterned localized crosslinking of the polymers by known thermal, chemical, ultraviolet and/or irradiation methods. Localized crosslinking of a polymer film may be achieved by masking of the to-be-left-as soluble film areas 10 prior to and during chemical, thermal or irradiation exposure. The non-soluble areas 11 are distributed, preferably, uniformly laterally and as a structurally integrated mesh along at least the top surface area of the first vapor permeable layer 3 with area sizes 0.01-20 mm, and coverage of 10-90% of total combined area of the top surface area of the first vapor permeable layer 3.

The first vapor permeable layer 3 may be made by coextrusion of a water soluble polymer as mentioned above and of a water resistant (nonsoluble) polymer (polypropylene, polyethylene, poly vinyl acetate, etc). In this case, the areas 11 of water resistant polymer are distributed, preferably, uniformly laterally along the first vapor permeable layer 3 with area sizes 0.01-20 mm, and 10-90% of total combined area.

Figure 3:
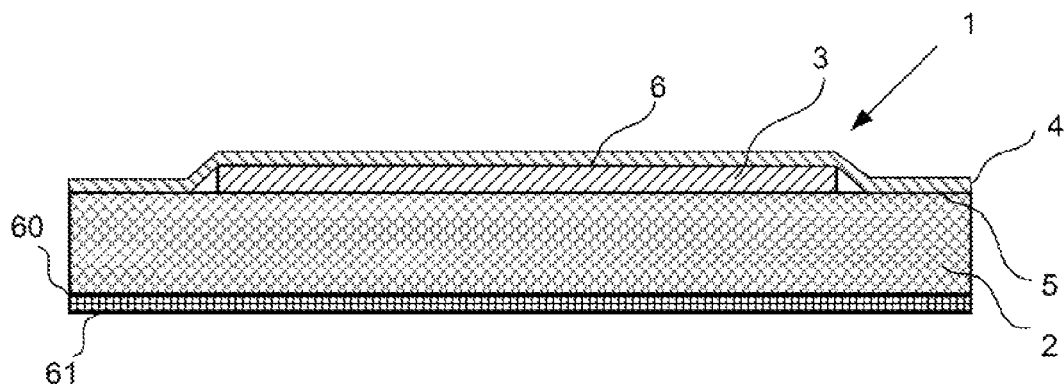
FIG. 3 is a schematic cross sectional view of another embodiment having a first vapor permeable layer spaced inwardly from the outer perimeter of a second and overlying vapor permeable layer.

In another embodiment, the periphery of the first vapor permeable layer 3 is spaced inwardly (as shown in FIG. 3) for 1-30 mm, preferably, 20 mm from the lateral outer perimeter of the second vapor permeable layer 4. The second vapor permeable layer 4 is directly bonded to the absorbing pad 2 near the periphery of the absorbing pad 2. In this case, since the periphery of the dressing is not covered by all of layers 3 and 4, but rather by a fewer number (e.g., one) of vapor permeable layers, the periphery of the dressing exhibits a higher MVTR and thus allows the periphery of the wound site to be drier than the core.

Figure 4:
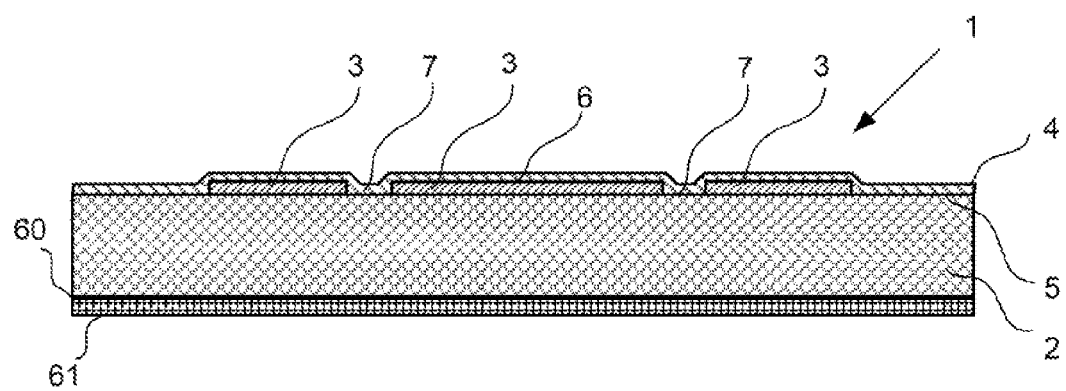
FIG. 4 is a schematic cross sectional view of another embodiment having a second vapor permeable layer attached to the absorbing core.

In another embodiment, the first vapor permeable layer 3 is provided with through openings 7 (FIG. 4). The openings 7 in layer 3 may have a lateral size (e.g., diameter of) 0.4-5 mm, and may be of various shapes, and may be uniformly distributed over the total lateral surface area consumed by the first vapor permeable layer 3. The combined area of the through openings 7 should be less than 20%, and more preferably less that 5%, of the consumed surface area of first vapor permeable layer 3. The second vapor permeable layer 4 is directly bonded to the absorbing pad 2 through the openings 7. The bonding adhesive used in openings 7 may be a porous one or a non-porous one depending on whether the dressing is designed to intentionally let vapors escape through the bonding openings 7 (and then through vapor permeable layer 4) or not.

Referring to FIG. 5, in another embodiment, an open cells, porous or perforated spacer layer 12 may be interposed between the first vapor permeable layer 3 and the second vapor permeable layer 4. Preferably, the spacer layer thickness is about 10-250 microns, the pore size 13 is 1-100 microns with 5-90% of open void area. The open cell pores or openings 13 may provide lateral liquid communication between each other. The spacer layer 12 may be made for example of a porous adhesive marketed by Adhesive Research, Inc. of Glen Rock, Pa.). The spacer layer 12 may be made by dots of an adhesive material that bonds with the first vapor permeable layer 3 and bonds with the second vapor permeable layer 4 (an example is MacTac™ glue dots marketed by MacTac, Inc. of Stow, Ohio). Although not specifically shown, the automatically-variable permeability layer 3 includes hydrolyzable material whereby its permeability at local spots to vapors and/or liquids changes when exposed for sufficiently long time to a hydrolyzing liquid (e.g., exudates). When a large concentration of exudates is present at a given sub-zone for a long time, the hydrolyzable layer 3 automatically breaks down at that location and then the exudate escapes through the broken down area to spread laterally into the pores of the porous or perforated spacer layer 12. This increases the lateral surface area by way of which vapors from the laterally spread liquid can permeate through vapor-permeable/liquid-impermeable layer 4 and out into the ambient. The rate of evaporation is thus automatically increased.

Referring to FIG. 6, in another embodiment, the function of the first automatically-variable permeability providing (AVPP) layer 3 may be provided by two or more spaced apart layers such as 15 and 16 separated from each other by an open cells porous or perforated spacer layer such as 17. Preferably, each layer 15 and 16 has a thickness of 10-250 microns, the pore size 20 is 1-100 microns with 5-90% of open void area. The respective MVTR variability characteristics of the spaced apart layers 15 and 16 need not be the same. The open cell pores or openings 20 of spacer layer 17 may provide lateral liquid communication between each other. The spacer layer 17 may be made of porous adhesive marketed by Adhesive Research, Inc., USA. The spacer layer 17 may be made by dots of an adhesive material that bonds well with each of layers 15 and 16 (an example is MacTac™ glue dots marketed by MacTac, Inc. USA). In the embodiment of FIG. 6, the spacer layer 12 between automatically-variable permeability layer 16 and vapor-permeable/liquid-impermeable layer 4 is also present.

In one embodiment, prior to employment at a wound site, the dressing 1 is packaged in a moisture and micro-organism impermeable pouch, sealed and pre and/or post sterilized by any of known in the art methods like gas sterilization or gamma or electron beam irradiation. The dressing packaging may include indicia identifying the dimensions, shapes MVTR ranges and liquid storage capacities of the enclosed dressing.

To apply the dressing to a wound, the user (e.g., health care provider) opens the sterile pouch, orients it so that the wound contact layer 60 faces the wound, and positions the lower surface 61 of the wound contact layer against the wound so that the wound center approximately coincides with the dressing center. The upper surface of the dressing may include centering indicia such as crosshair lines that may be lined up with crosshair line extensions drawn on healthy areas of the patient's skin outside of the per-wound areas.

In the case of FIGS. 3-6 where the second vapor permeable layer 4 extends peripherally beyond the first vapor permeable layer 3 so that a higher MVTR is provided in the peripheral areas of the wound site, the moisture (e.g., water vapor) output from the peri-wound skin area is rapidly exhausted through the areas covered only by the first vapor permeable layer 3 so that the healthy skin area surrounding the wound site remains relatively dry. An occasional droplet of perspiration generated at the peri-wound skin or healthy skin area may be is absorbed by the co-extent absorbent pad 2 and thereafter evaporated through the immediately overlying second vapor permeable layer 4 of the peripheral zone. As a result, the mini-environment over the peri-wound and healthy skin areas remain appropriately dry without accumulation of skin-damaging liquid thereat. This helps prevent skin maceration.

If an encountered wound is identified as low exuding or has no exudates (low drainage), the limited moisture (exudate, secretion, water vapor) from the wound bed is absorbed by the absorbent pad 2 but moisture vapor evacuation (exhaust) from over the wound bed and out to the ambient air is constrained by the presence of the non-hydrolyzed first vapor permeable layer 3 which initially has a relatively low MVTR and stays in that state if not hydrolyzed by absorbed and upwardly drawn exudates. As a result, when the encountered wound zone conditions are that of there being no or relatively low levels of exudates, the initially low MVTR of the automatically-variable permeability layer 3 remains low, the micro-environment over the wound bed is therefore kept moist and of a relatively high-humidity where the latter prevents desiccation of the surface of the wound bed and this facilitates optimal conditions for inward cell growth proliferation (from the surrounding peri-wound areas) and thus rapid wound healing. The presence of the low MVTR, first vapor permeable layer 3 over the peri-wound areas also supports a relatively high or medium humidity environment over the wound edge and this helps to prevent wound edge desiccation and/or damage to newly epithelialized skin.

If, on the other hand, a given part of a wound site is highly exuding (high liquid production rates), the exudates are absorbed by the absorbent pad 2 over that part of the wound site and drawn up into contact with the automatically-variable permeability layer 3. The vapor evacuation (exhaust to the outside) is initially slow in this region because of the vapor flow restricting, serial combination of the first and second moisture vapor permeable layers 3 and 4, where the serial combination exhibits a low combined MVTR. As absorption begins, the water portion of the exudates mixture is initially bound to the superabsorbent or hydropolymer particles of fibers in the absorbing core of pad 2 so that initially there are no free flowing water particles in the pores between the superabsorbent particles and fibers.

If and when the amount of liquid absorbed by the pad 2 becomes sufficiently large after some time (e.g., after the dressing is worn by the patient for a predetermined number of hours), the absorbed liquid saturates the water binding capacity of the water-binding material and subsequently, free-flowing (unbound) water will appear in the spaces between the water-binding particles and/or fibers of the absorbent pad 2. Eventually this unbound liquid rises to and reaches the first vapor permeable layer 3. In the case where the first vapor permeable layer 3 includes the hydrolyzable material spots 10, exposure of these spots 10 to the free flowing liquid (e.g., water, exudates) in growing amounts triggers disintegration (dissolving) of the hydrolyzable parts of the first vapor permeable layer 3, where this disintegration adaptively occurs generally over only the heavily exuding parts of the wound site and not over the non-exuding or lightly exuding parts. In one variation, the absorbent pad 2 is provided with an anisotropic absorbency profile, for example at least partly up in the upper heights of the absorbent pad 2 so that the liquids from the heavily exuding parts of the wound site are inhibited from cross flowing laterally through the absorbent pad 2 to cause unintended disintegration of the hydrolyzable material spots 10 that are disposed over the drier micro-zones of the wound site. As a result, the drier micro-zones are prevented from becoming too dry due to excessive vapor exhaust (into the ambient) over their respective areas while the heavily exudating micro-zones of the wound site are prevented from becoming too wet thanks to the automatically increased vapor exhaust rates (into the ambient) caused by selective disintegration of the hydrolyzable material spots 10 that are disposed over the wetter micro-zones. In one embodiment, the hydrolyzable material spots 10 are not homogenous over each micro-zone but rather distributed as faster dissolving (more readily disintegrating) and more slowly dissolving spots 10 so that the automatically induced increase of MVTR will be automatically proportional to the length of time that the spots 10 of different hydrolyzing rates are exposed to hydrolyzing liquid and or to the concentration levels and/or chemistries (e.g., alkalinity) of the locally present hydrolyzing liquids. In other words, once the vapor exhaust rate of a given micro-zone increases to match the liquid production rate of its underlying portion of the wound site, the liquid concentration levels in that subregion drop so as to no longer expose the remaining spots 10 (those with slower hydrolyzing rates) to a hydrolyzing concentration of the liquid and the automatic process of progressively disintegrating more and more of the harder-to-hydrolyze material spots 10 automatically comes to a substantial stop. Thus each micro-zone of the wound site is automatically kept from becoming either too wet or too dry.

In the case of the spacer-including structures of FIGS. 5-6, even if a given micro-zone in the wound site is both small in area and high in exudation rate, when the excess liquid crosses through the first vapor permeable and also converted-into-being a liquid permeable layer 3, the permeating-through liquid spreads out to cover a larger lateral surface area by passing through the open cell pores of the spacer layer(s) 12 and/or 17 so that the spread out liquid is provided with a larger upper surface area from which its vapors may evaporate into the ambient by way of the liquid impermeable but vapor permeable layer 4. In other words, since the second vapor permeable layer 4 is liquid impermeable, when the liquid gets into the natural capillaries or gaps, formed by spacer 12 between the first and second vapor permeable layers 3 and 4, the liquid spreads out laterally. Then, however, the liquid impermeable layer 4 blocks the liquid from leaking out to the outside of the dressing. However, because of the MVTR of the second vapor permeable layer 4 is high, the evaporation rate of water vapor through the upper, second vapor permeable layer 4 sharply increases due to the expanded lateral surface area provided for such evaporation and as a consequence, this reduces the accumulation rate of liquids in portions of the absorbing core 2 that overlie heavily exudating micro-zones of the wound site even if those heavily exudating micro-zones, on their own, have relatively small surface areas.

By providing the first vapor permeable layer 3 of FIG. 6 as being made of a combination of two or more spaced apart soluble films 15 and 16 with porous spacers in between, a more gradual increase of the rate of water vapor evaporation from the dressing may be provided for. More specifically, the rising liquid spreads out laterally in area by a first proportional amount when it reaches the lower spacer layer 17 and then the reduced concentration of liquid controls the subsequent disintegration of the hydrolyzable material spots 10 (not shown) of permeable layer 16. Yet more specifically, a time delay function may be provided wherein; if the wound exuding intensity was high for a short time immediately after the wound was created and then it later becomes much reduced, then only one layer 15 is dissolved by immediate exposure to the high concentrations of exudating liquid, and due to time delay in the liquids advancing to the next successive layer 16, its respective hydrolyzable material spots 10' (not shown) will remain more intact and thus prevent too high of a water evaporation rate from developing where such a too-high of an evaporation rate can lead to undesired wound part over-desiccation.

The material of the first vapor permeable layer 3 may form a viscous liquid when it is fully disintegrated by the hydrolyzing liquid(s) of sufficient concentration. After the hydrolyzing liquid(s) recede (due to evaporation of their water component for example), the left-behind viscous liquid formed by the fully dissolved hydrolyzable material spots 10 (not shown) is confined to remaining between, and drying out between the absorbing pad 2 and the second vapor permeable, but liquid impermeable layer 4. If the intensity of wound exudates discharge rate next becomes reduced, the dried out remnants of the viscous liquid will, upon completion of their drying out process, automatically form a nonporous film that works to reduce further water vapor loss from the absorbing pad 2 at that spot and ultimately reduce moisture loss from the less-exuding wound bed thus automatically providing for a moist environment for the underlying wound site subregions even if beforehand, those subregion were heavily exuding ones and now they are less exuding ones. Small pores of the spacers 12, 17 and the bonding layer between the absorbing pad 2 and the first vapor permeable layer 3 help to distribute the high viscous liquid more uniformly by locking the liquid in the pores. That results in forming more uniform, vapor blocking films as drying of the viscous liquid pools occurs.

When the lateral spacer layers (e.g., 12 and/or 17) are present, even if the first vapor permeable layer 3 is dissolved as a small spot only over a small, but heavily exuding part of the wound site, the rising column of exudate liquid will be driven up by capillary forces through the one small spot so as to be is quickly spread out laterally into a much larger lateral area between the first and second vapor layers 3 and 4 by action of the one or more spacer layers. This process significantly increases the area of evaporation through the second vapor permeable layer 4. In other words, the relatively high MVTR of the second vapor permeable but liquid impermeable layer 4 combined with the larger evaporation surface area provided to the laterally spreading out portions of the rising column of liquid exudate provides a relatively high water evaporation rate, that then automatically reduces liquid accumulation in the absorbing core 2 and increases the useful wear time of the dressing 1. As a consequence, dressings in accordance with the present disclosure need not be changed as often as the non-adaptive traditional dressings and costs of providing health care services may be significantly reduced.

By spacing the edge of the first vapor permeable layer 3 laterally inward relative to the dressing 1 edge (e.g., FIG. 3), the healthy skin around the wound site is preserved and the wear time of the dressing may therefore be increased. One of reason for frequent dressing changes may be that undesired leakage of exudates from the dressing periphery (edge) tends to damage the surrounding healthy skin. However, in the embodiments where the first vapor permeable layer 3 is spaced inward from the dressing edge, lateral spreading of exudate liquid between the layers 3 and 4 is blocked from occurring at the dressing edge. This prevents undesirable leakage of a potentially corrosive and infectious liquid (e.g., bacteria containing exudate) from the dressing edge where such leakage may then require more frequent wound cleanings and more frequent change of the dressing even before the absorbing core 2 reaches the limits of its absorbing capacity. In other words, the full exudate absorbing capacity of the absorbent pad 2 may be exploited due to a combination of advantageous operations of the here disclosed, automatically-adaptive wound dressing 1. Excess moisture is quickly evaporated away as needed so that the absorbent pad 2 does not become prematurely saturated with water and damaging leakage of exudate to the healthy skin surrounding the wound site is prevented so that the frequency of dressing changes may be reduced. In the mean time, the absorbent pad 2 collects and stores the non-water components of the wound site exudates to basically the full exudate absorbing capacity of the absorbent pad material. Hence, the absorbing capacity is efficiently utilized to its full extent.

It is possible for the laterally spreading liquid between the first and second vapor permeable layers 3 and 4 to fully disintegrate the first vapor permeable layer 3 if the latter layer is fully hydrolyzable. That may result in undesirable delamination of dressing layers and loss of dressing integrity. Therefore in at least some of the illustrated embodiments (e.g., FIG. 2), the non-hydrolyzable (e.g., water resistant) segments 11 are provided so as to define an integrity maintaining mesh that keeps the first vapor permeable layer 3 well bonded to the underlying absorbing pad 2 and keeps the second vapor permeable layer 4 also bonded to the structure, thus preventing loss of dressing integrity. Although not shown in the other figures, it is to be understood that the concept of the integrity maintaining mesh 11 is equally applicable in those other embodiments. Alternatively or additionally the illustrated bonding in FIG. 4 of the second vapor permeable layer 4 directly to the absorbing pad 2 through the provided bonding openings 7 provides another means of maintaining dressing integrity. One or both of these integrity maintaining techniques may be used in the others of the illustrated embodiments.

If the first vapor permeable layer 3 is made of a material that is soluble only in warm water (temperature >25° C.), then the triggering of dissolution of the first vapor permeable layer is the results of the simultaneous effects of two factors: presence of free flowing liquid between the superabsorbent particles and fibers, and the temperature >25° C. (preferably 28-32° C.) of the first vapor permeable layer 3.

A wound bed tissue temperature is close to the normal human body temperature of 36.6° C. Moreover, the fibrous or foam structure of the absorbing pad 2 defines is a relatively good thermal insulator. As a result, a significant temperature gradient tends to develop between the wound bed tissue and the first vapor permeable layer 3; for example with temperature dropping from 36.6° C. (or higher if the patient has a fever) to ambient room temperature as vertical distancing away from the wound bed tissue and closer to the vapor-permeable/liquid-impermeable layer 4 progresses for rising droplets of exudate liquid. As a result, if no warm exudate rapidly rises through the absorbent pad 2, the temperature of the first vapor permeable layer 3 remains close to the ambient temperature (usually room temperature 18-22° C.) and the automatically-variable permeability layer 3 is not converted into it high MVTR mode. On the other hand, if the wound site is heavily exuding warm liquid and that warm (above room temperature) liquid rapidly reaches the first vapor permeable layer 3, the latter layer 3 quickly disintegrates at that spot and allows for high rates of vapor release.

When all the absorbed liquid is bounded to superabsorbent particles and fibers and no free flowing water has yet formed, there are still a lot of air in the empty cells between fibers and particles of the absorbing pad 2, the thermal insulation characteristics of the pad 2 are preserved and a significant difference in temperature continues to exist between the wound bed and the first vapor permeable layer 3 temperature. This maintained thermal insulation helps to assure that a correspondingly lower temperature is maintained at least for a while for parts of the first vapor permeable layer 3 that are disposed over non-exuding or low-exuding zones of the wound site. Accordingly, even if a column of warm exudate breaks through one part of layer 3 and spreads laterally between the first and second layers, 3 and 4, and over the non-exuding or lesser exuding parts of the wound site, a cooling of the upwelling warm and spreading out exudate occurs due to water evaporation and heat conductivity to the ambient air through the liquid-impermeable but vapor breathing (LIVB) layer 4 and also due to thermal inertia whereby the laterally spaced apart areas of layer 3 are initially kept cool helps to prevent undesired disintegration of the first vapor permeable layer 3 over the these non- or less-exuding parts in spite of the presence of laterally spreading out liquid between the first and second layers, 3 and 4, and over these parts of the wound dressing. In other words, the temperature-dependent disintegrating characteristics of the automatically-variable permeability layer 3 help to provide for the following: a) to continue providing a controlled moist air environment over the non-exuding parts of the wound due to the still intact first vapor permeable layer 3 above them; b) to reduce the probability of over-wetting of non-exuding wound parts and/or peri-wound skin and/or surrounding healthy skin due to the blocking of undesired leakage of the excessive liquid from the heavily exuding wound part and into contact with the drier parts; d) to reduce or minimize the probability of infection or re-infection of the non-exuding (e.g., more healed) wound parts and peri-wound skin due to bacteria being transferred together with the spread out exudate liquid from the exuding wound part.

Figure 7:
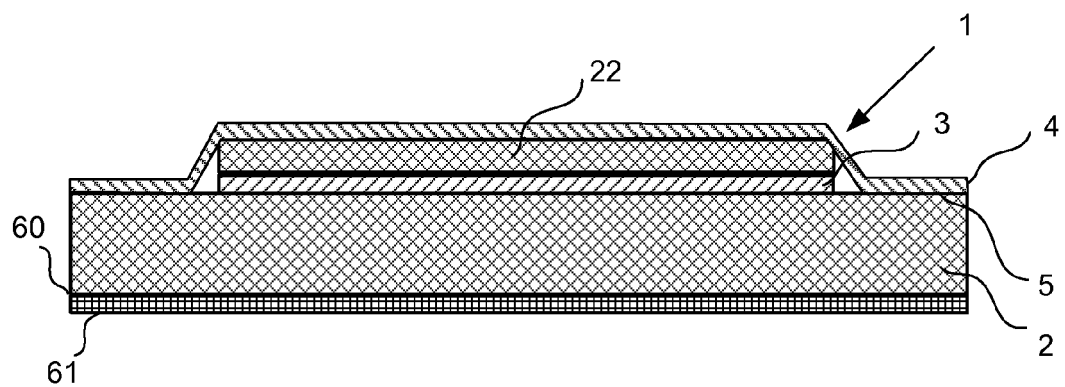
FIG. 7 is a schematic cross sectional view of a further embodiment having a second absorbing layer disposed above the automatically-variable permeability providing (AVPP) layer.

Referring to FIG. 7, shown here is another embodiment, similar to that of FIG. 5 except that in FIG. 7, a second liquid absorbing layer 22 is disposed above and in contact with the automatically-variable permeability providing (AVPP) layer 3. The second liquid absorbing layer 22 may be made of same or similar materials as that the first liquid absorbing layer 2 (a.k.a. absorbent pad 2) and/or of different materials. The second liquid absorbing layer 22 may be of a homogeneous composition laterally thereacross and/or vertically therethrough or it may vary in composition and/or absorbency characteristics either laterally thereacross, or vertically therethrough or in both senses. The thickness and/or absorbency capacity of the second liquid absorbing layer 22 need not be the same as that of the first liquid absorbing layer 2 (a.k.a. absorbent pad 2) and at least in one embodiment, the second liquid absorbing layer 22 is thinner and has a lower absorbency capacity.

One possible function for the second liquid absorbing layer 22 is to draw fluids (e.g., permeability altering liquids and/or vapors) away from the top side of the automatically-variable permeability providing (AVPP) layer 3 such that the permeability of AVPP layer 3 is controlled essentially by the concentration, amounts and/or chemistries of the fluids (e.g., permeability altering liquids and/or vapors) transmitted to its lower side by the first liquid absorbing layer 2 (a.k.a. absorbent pad 2) and not substantially by fluids that appear near the upper side of the AVPP layer 3. With that said, it is nonetheless within the present contemplation of the disclosure that in an alternate embodiment, fluid concentrations at the upper side of the first AVPP layer 3 (e.g., those representative of humidity in the ambient air) do alter the permeability of the first AVPP layer 3 (or alternatively of a second AVPP layer such as layer 16 of FIG. 6). In the case where the function of the second liquid absorbing layer 22 is to draw fluids vertically away from the upper surface of the first AVPP layer 3 of FIG. 7, the absorbency of the material in the second liquid absorbing layer 22 may increase as one progresses vertically up through that layer 22 as shown in FIG. 7. Capillary action may quickly pull permeability-affecting fluids away from the top side of the first AVPP layer 3 and towards proximity with the liquid-impermeable but vapor breathing (LIVB) layer 4 above it so that vapors from the vertically drawn up fluids exhaust into the ambient air by way of LIVB layer 4. As in the case of FIG. 6, it is within the contemplation of the present disclosure to have two or more spaced apart automatically-variable permeability providing (AVPP) layers (e.g., like 15 and 16 of FIG. 6), where in the case of FIG. 7 (or that of next described FIG. 8) the second AVPP layer (not shown in FIGS. 7-8) is disposed above the second liquid absorbing layer 22 (and/or above the lateral fluids dispersing layer 17 of FIG. 8). That second AVPP layer (not shown in FIGS. 7-8) would respond variably to the concentration, amounts and/or chemistries of the fluids (e.g., permeability altering liquids and/or vapors) transmitted to its lower side by the second liquid absorbing layer 22 (and/or the lateral fluids dispersing layer 17 of FIG. 8).

Figure 8:
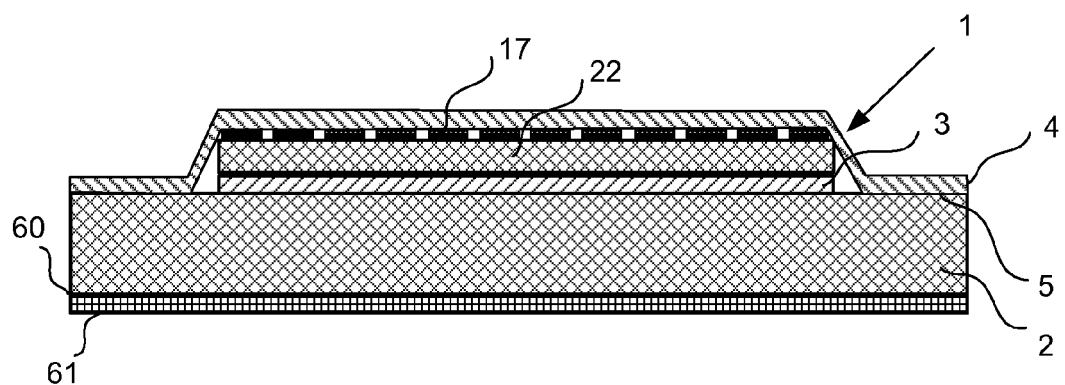
FIG. 8 is a schematic cross sectional view of yet a further embodiment having a fluids lateralizing layer disposed above the second absorbing layer.

Referring to FIG. 8, shown here is a further embodiment, similar to that of FIG. 7 except that in FIG. 8, a lateral fluids dispersing layer 17 (e.g., similar to 17 or 12 of FIG. 6) is provided above the second liquid absorbing layer 22. Once absorbing layer 22 has drawn fluids vertically up and away from the first AVPP layer 3, the lateral fluids dispersing layer 17 distributes those vertically transmitted fluids (e.g., liquids and/or vapors) laterally over a wider surface area so that vapors of these may more quickly be exhausted into the ambient air by way of liquid-impermeable but vapor breathing (LIVB) layer 4.

It is to be appreciated that the above are merely illustrative examples and that those skilled in the art, after having appreciated the present disclosure, will be enabled into seeing many additional variations. In general, one of the aspects taught herein is that one or more automatically-variable permeability providing (AVPP) layers like 3 and/or 15-16 may be provided above a wound site having respective microzones that exhibit different tissue types (e.g., heavily exuding, lightly exuding, epithelializing, etc.); that fluids representative of the current states of those respective micro-zones may be vertically transmitted up to corresponding sub-portions of at least the first AVPP layer 3 where the first AVPP layer 3 is structured to variably alter its permeability in the corresponding sub-portions according to the concentration, amounts and/or chemistries of the fluids (e.g., permeability altering liquids and/or vapors) transmitted at least to its lower side, and as a result; a wound site treatment mechanism is provided that variably responds to the tissue-type representing fluidic signals sent to it from the respective micro-zones of the wound site below.

WORKING EXAMPLES

Example 1

A wound dressing in accordance with the disclosure was made by laminating of the following layers: 1) a wound contact layer 61 made of cross-linked polyvinyl alcohol fibers, the polymer was blended with antimicrobial additive polyhexamethylene biguanide (PHMB) 0.3 w %, the layer thickness was 150 microns, the layer density was 0.1 g/cm3, the fiber diameter range was 0.5-2 micron; 2) the absorbent pad 2 was made of polyester fibers with super-absorbent polymer particles (material being designated as WoundFelt™ marketed by National Nonwoven, Inc, Easthampton, Mass.), the layer thickness was 1.2 mm; 3) the first vapor permeable layer 3 was made of polyvinylpyrrolidone (marketed by Scientific Polymers, Inc, USA), had a thickness of 150 microns, an initial MVTR of 400 g/m2/24 hours when dry; 4) the second vapor permeable layer 4 was made of polyurethane high MVTR film (Bioflex™, marketed by SCAPA corporation, USA), had a film thickness of 25 microns, an MVTR of 2500 g/m2/24 hours). The layers 61, 2, 3 and 4 were permanently bonded to each other by patterned pressure sensitive adhesive (Rx560U™, marketed by SCAPA corporation, USA). The size of the so-fabricated dressing was 100×100 mm, the shape was a square with rounded corners having a radius of 15 mm.

Example 2

The wound dressing per Example 1 and further modified such that the absorbent pad 2 contained a pre-charge of sterile water at a density of 0.15 g/cm2 and glycerin at 0.03 g/cm2.

Example 3

The wound dressing per Example 2 further modified such that the first vapor permeable layer 3 was made of two polyvinylpyrrolidone films (marketed by Scientific Polymers, Inc, USA) each having a thickness of 150 microns, and an MVTR of 400 g/m2/24 hours when dry. The films were bonded to each other by a porous adhesive (marketed by Adhesive Research, Inc., Glen Rock, Pa.) having a thickness of 50 microns, a pore size of 20-250 microns, and an open area percentage equal to about 40%.

The present disclosure is to be taken as illustrative rather than as limiting the scope, nature, or spirit of the subject matter claimed below. Numerous modifications and variations will become apparent to those skilled in the art after studying the disclosure, including use of equivalent functional and/or structural substitutes for elements described herein, use of equivalent functional couplings for couplings described herein, and/or use of equivalent functional steps for steps described herein. Such insubstantial variations are to be considered within the scope of what is contemplated here. Moreover, if plural examples are given for specific means, or steps, and extrapolation between and/or beyond such given examples is obvious in view of the present disclosure, then the disclosure is to be deemed as effectively disclosing and thus covering at least such extrapolations.

Reservation of Extra-Patent Rights, Resolution of Conflicts, and Interpretation of Terms After this disclosure is lawfully published, the owner of the present patent application has no objection to the reproduction by others of textual and graphic materials contained herein provided such reproduction is for the limited purpose of understanding the present disclosure of invention and of thereby promoting the useful arts and sciences. The owner does not however disclaim any other rights that may be lawfully associated with the disclosed materials, including but not limited to, copyrights in any computer program listings or art works or other works provided herein, and to trademark or trade dress rights that may be associated with coined terms or art works provided herein and to other otherwise-protectable subject matter included herein or otherwise derivable herefrom.

If any disclosures are incorporated herein by reference and such incorporated disclosures conflict in part or whole with the present disclosure, then to the extent of conflict, and/or broader disclosure, and/or broader definition of terms, the present disclosure controls. If such incorporated disclosures conflict in part or whole with one another, then to the extent of conflict, the later-dated disclosure controls.

Unless expressly stated otherwise herein, ordinary terms have their corresponding ordinary meanings within the respective contexts of their presentations, and ordinary terms of art have their corresponding regular meanings within the relevant technical arts and within the respective contexts of their presentations herein. Descriptions above regarding related technologies are not admissions that the technologies or possible relations between them were appreciated by artisans of ordinary skill in the areas of endeavor to which the present disclosure most closely pertains.

Given the above disclosure of general concepts and specific embodiments, the scope of protection sought is to be defined by the claims appended hereto. The issued claims are not to be taken as limiting Applicant's right to claim disclosed, but not yet literally claimed subject matter by way of one or more further applications including those filed pursuant to 35 U.S.C. §120 and/or 35 U.S.C. §251.

What is claimed is:

1. An adaptive wound dressing comprising:
   a liquid absorbing pad having respective upper and lower major surfaces;

a liquid-impermeable but vapor breathing (LIVB) layer disposed above the liquid absorbing pad; and a first automatically-variable permeability providing (AVPP) layer interposed between the liquid absorbing pad and the LIVB layer;

wherein the first AVPP layer has a capability to automatically change at least in terms of a respective degree of fluid permeability provided by at least one portion thereof to a first class of fluids when that at least one portion thereof is subjected to at least one of the same first class of fluids or to a different second class of fluids in sufficient quantity and/or concentration and/or for a sufficient length of time; and wherein said automatic change capability of the at least one portion of the first AVPP layer with regard to the degree of fluid permeability of the at least one portion of the first AVPP layer includes a capability to change whereby the at least one portion of the first AVPP layer initially switches from having a first permeability corresponding to a relatively low, first vapor transmission rate, to having a second permeability corresponding to a relatively higher and second vapor transmission rate, and to thereafter switching from having the second permeability to having a third permeability corresponding to a third vapor transmission rate that is lower than the second vapor transmission rate.

2. The adaptive wound dressing of claim 1 wherein:

said automatic change capability of the at least one portion of the first AVPP layer with regard to the degree of fluid permeability provided by the at least one portion of the first AVPP layer includes switching from being impermeable to liquids to being permeable to liquids.

3. An adaptive wound dressing comprising:

a liquid absorbing pad having respective upper and lower major surfaces;

a liquid-impermeable but vapor breathing (LIVB) layer disposed above the liquid absorbing pad; and a first automatically-variable permeability providing (AVPP) layer interposed between the liquid absorbing pad and the LIVB layer;

wherein the first AVPP layer has a capability to automatically change at least in terms of a respective degree of fluid permeability provided by at least one portion thereof to a first class of fluids when that at least one portion thereof is subjected to at least one of the same first class of fluids or to a different second class of fluids in sufficient quantity and/or concentration and/or for a sufficient length of time; and wherein the at least one portion of the first AVPP layer initially has a nonporous first micro-structure of a first predetermined thickness that is permeable to vapor but not to liquids.

4. The adaptive wound dressing of claim 3 wherein:

the at least one portion of the first AVPP layer responds to being subjected to at least one of the first and second classes of fluids by switching from having said initial nonporous first micro-structure of the first predetermined thickness to having a post-exposure nonporous second micro-structure of a smaller second thickness that is more permeable to vapor but still not permeable to liquids.

5. An adaptive wound dressing comprising:

a liquid absorbing pad having respective upper and lower major surfaces;

a liquid-impermeable but vapor breathing (LIVB) layer disposed above the liquid absorbing pad; and a first automatically-variable permeability providing (AVPP) layer interposed between the liquid absorbing pad and the LIVB layer;

wherein the first AVPP layer has a capability to automatically change at least in terms of a respective degree of fluid permeability provided by at least one portion thereof to a first class of fluids when that at least one portion thereof is subjected to at least one of the same first class of fluids or to a different second class of fluids in sufficient quantity and/or concentration and/or for a sufficient length of time; and wherein said automatic change capability of the at least one portion of the first AVPP layer with regard to the degree of fluid permeability is a temperature dependent one.

6. The adaptive wound dressing of claim 5 wherein:

the automatic change capability provided by the at least one portion of the first AVPP layer is one that does not initially occur until the respective at least one portion of the first AVPP layer is subjected to at least one of the first and second classes of fluids and while at a minimum temperature greater than at least 20 degrees C.

7. The adaptive wound dressing of claim 6 wherein:

the minimum temperature is at least 28 degrees C.

8. The adaptive wound dressing of claim 6 wherein:

the minimum temperature is at least 32 degrees C.

9. An adaptive wound dressing comprising:

a liquid absorbing pad having respective upper and lower major surfaces;

a liquid-impermeable but vapor breathing (LIVB) layer disposed above the liquid absorbing pad; and a first automatically-variable permeability providing (AVPP) layer interposed between the liquid absorbing pad and the LIVB layer;

wherein the first AVPP layer has a capability to automatically change at least in terms of a respective degree of fluid permeability provided by at least one portion thereof to a first class of fluids when that at least one portion thereof is subjected to at least one of the same first class of fluids or to a different second class of fluids in sufficient quantity and/or concentration and/or for a sufficient length of time; and wherein an initial fluid permeability provided by the least one portion the first AVPP layer before automatically changing in degree of fluid permeability provided to the first class of fluids is about or less than 1000 g/m$^2$/24 Hours.

10. The adaptive wound dressing of claim 9 wherein:

a subsequent fluid permeability provided by the least one portion the first AVPP layer after automatically changing in degree of fluid permeability provided to the first class of fluids is substantially greater than 1000 g/m$^2$/24 Hours.

11. An adaptive wound dressing comprising:

a liquid absorbing pad having respective upper and lower major surfaces;

a liquid-impermeable but vapor breathing (LIVB) layer disposed above the liquid absorbing pad; and a first automatically-variable permeability providing (AVPP) layer interposed between the liquid absorbing pad and the LIVB layer;

wherein the first AVPP layer has a capability to automatically change at least in terms of a respective degree of fluid permeability provided by at least one portion thereof to a first class of fluids when that at least one portion thereof is subjected to at least one of the same first class of fluids or to a different second class of fluids in sufficient quantity and/or concentration and/or for a sufficient length of time; and wherein prior to operatively engaging with a wound site, the liquid absorbing pad has one or more initial pre-charge liquids or gels embedded therein.

12. The adaptive wound dressing of claim 11 wherein:
the one or more initial pre-charge liquids or gels embedded in the liquid absorbing pad includes at least one of a hygroscopic liquid, a sterile saline solution, water, and an antimicrobial liquid or gel.

13. The adaptive wound dressing of claim 12 wherein:
the one or more initial pre-charge liquids or gels embedded in the liquid absorbing pad includes glycerin as a component thereof.

14. The adaptive wound dressing of claim 11 wherein:
a quantity of the one or more initial pre-charge liquids or gels embedded in the liquid absorbing pad prior to said operative engagement with a wound site is less than a maximum liquid absorbing capacity of the liquid absorbing pad.

* * * * *